United States Patent [19]
Akinmade et al.

[11] Patent Number: 5,411,584
[45] Date of Patent: May 2, 1995

[54] DENTAL CEMENT

[75] Inventors: Ademola O. Akinmade, Mitcham; Julian H. Braybrook, Ewell, both of England

[73] Assignee: British Technology Group Limited, London, England

[21] Appl. No.: 256,265

[22] PCT Filed: Feb. 10, 1993

[86] PCT No.: PCT/GB93/00272

§ 371 Date: Jul. 1, 1994

§ 102(e) Date: Jul. 1, 1994

[87] PCT Pub. No.: WO93/16675

PCT Pub. Date: Sep. 2, 1993

[30] Foreign Application Priority Data

Feb. 19, 1992 [GB] United Kingdom ............... 9203510

[51] Int. Cl.$^6$ ............................................. C09K 3/00
[52] U.S. Cl. ........................................ 106/35; 523/116
[58] Field of Search ............. 106/35; 523/116; 524/2, 524/5, 123, 130, 414, 433, 430, 492, 493, 494

[56] References Cited

U.S. PATENT DOCUMENTS

| | | | |
|---|---|---|---|
| 4,758,612 | 7/1988 | Wilson et al. | 523/116 |
| 5,079,277 | 1/1992 | Wilson et al. | 523/116 |
| 5,179,135 | 1/1993 | Ellis et al. | 523/116 |

FOREIGN PATENT DOCUMENTS

| | | |
|---|---|---|
| 0225706 | 6/1987 | European Pat. Off. . |
| 0340016 | 11/1989 | European Pat. Off. . |
| 0431740A1 | 6/1991 | European Pat. Off. . |

*Primary Examiner*—Helene Klemanski
*Attorney, Agent, or Firm*—Nixon & Vanderhye

[57] ABSTRACT

A poly(vinyl phosphonic acid)/glass cement is improved by pre-reacting the acid with $ZnF_2$ and $BPO_4$, and by mixing $BPO_4$ with the glass powder.

22 Claims, No Drawings

DENTAL CEMENT

This invention relates to a dental cement made from a polymeric phosphonic acid and a glass, other metal oxide or cermet, to a method of making the cement and to materials for use in making the cement.

Such cements are described in GB-A-2219289 and it would be desirable to increase their compressive strength and to lengthen their working time.

According to the present invention, a cement composition comprises an intimately blended mixture of a water-containing liquid, at least 30% by weight of the composition being a cation-catalysed cross-linkable polymeric acid containing on average one phosphonic acid group per one to three backbone carbon atoms, such as poly(vinyl phosphonic acid) PVPA optionally containing poly(acrylic acid), and a metal oxide (e.g. ZnO) or cation-leachable surgically acceptable aluminosilicate (preferably fluoroaluminosilicate) glass powder preferably containing $SiO_2$ and $Al_2O_3$ in the mass proportions (0.6 to 3.0):1 such as (1 to 2):1, preferably (1½ to 2):1, in the proportions (1 minus x)g phosphonic acid: 1 to 5 g glass: x g liquid, where x is from 0.3 to 0.7, characterised in that the acid has been pre-reacted in aqueous solution at elevated temperature with a fluoride and/or phosphate of preferably a divalent or trivalent metal e.g. of Zn, Sn, Mg, Ca, Al or B, or a mixture, e.g. $ZnF_2+BPO_4$, preferably amounting to 2½ to 12½% (e.g. 4 to 8%) by weight of said acid, preferably in the presence of water, preferably present as solvent of the acid.

The glass powder is preferably two-phase and preferably consists of particles substantially all of which are smaller than 100 microns, preferably smaller than 60 microns. If it is desired to reduce its reactivity with the acid, the glass powder may be heat-treated, for example at at least 400° C. (preferably 450°–600° C.) for at least 40 minutes (preferably at least 55 minutes).

While a glass rapidly quenched from a high temperature will usually be translucent, certain heat treatments yield an opaque glass, and hence an opaque cement, which may be acceptable in appropriate cases. The glass may alternatively be de-activated by washing in a dilute acid such as acetic acid, typically in a 2½% weight concentration for 1 hour. Advantageously, the glass is admixed (e.g. by grinding together) with boron phosphate, in a preferred amount based on the glass of at least 10 wt %, more preferably 12–20 wt %. In place of glass, MgO deactivated at at least 900° C. may be used.

The solvent is preferably water, and preferably dissolves the acid, the glass being kept separate until use. However, the acid may be pre-reacted and dried (optionally freeze-dried but more preferably spray-dried) and mixed with the glass; the invention extends to this mixture, and to a pack of dried acid plus glass, preferably packed in a sealed capsule (PVPA being hygroscopic) and which is made into cement by adding the said liquid. The acid may be accompanied by a desiccant such as hydrophobic silica. In a modification, the glass may be replaced by a metal oxide such as ZnO or MgO, preferably heat-treated, preferably of dense powder morphology, or by a cermet. (A cermet is a metallised glass powder, typically formed by fusing (by sintering) a metal powder (e.g. silver or tin) onto the surface of a glass powder, and may offer lower friction when burnished and greater wear resistance than glass in these cements.) A chelating agent e.g. a chelating phosphonic acid is preferably present, in a preferred amount of 10 to 20% by mass.

The invention extends to a pack comprising two pastes which when mixed form a cement composition as set forth above; the first paste may be the pre-reacted acid(s) plus water, and the second paste may be the glass or oxide powder suspended in aqueous thickening agent e.g. methylcellulose. Ordinary aqueous PVPA with optional complexant (described later) is a solution and therefore not entirely satisfactory as a paste, but pre-reacted PVPA as set forth above forms a gel and thus a true paste. If the two pastes have been formulated to appropriate concentrations, one could in use squeeze out equal lengths of paste from two tubes, or scoop out equal numbers of spoonfuls from two tubs, as an easy way to ensure that the mixture is of the correct composition.

The composition may further contain acid-neutralising agents such as zinc oxide or aluminium phosphate or both, in a total amount of up to 10% by mass based on the acid solution, and/or complexing agents such as phosphonic-acid-based materials.

The invention also extends to a pack comprising the components of the cement composition set forth above, so packed that when unpacked and mixed they form the cement.

Inadequate chelating phosphonic acid will inadequately lengthen the working time, while excess chelating phosphonic acid will compete with the polymeric phosphonic acid in forming a reaction cement with the glass, the cement formed by "chelating" acid being a source of potential weakness.

The invention will now be described by way of example.

The ingredients of a cement composition according to the invention comprise glass, glass modifier, acid (PVPA), prereactant, desiccant, complexant, and solvent. These will be considered in turn.

Glass: Three compositions of glass were used, referred to for convenience as G4, G5 and G6.

G4 and G5 are prepared by mixing together 424 parts by weight silica, 32 parts by weight alumina, 18 parts by weight calcium fluoride, 24 parts by weight cryolite $Na_3AlF_6$ and 8 parts by weight aluminium phosphate. G4 is fired at 1330° C., held for 70 minutes, then quenched <poured) straight into water. G5 is fired at 1280°–1300° C., held for 90 minutes, poured out of the furnace onto a metal plate and held there as a melt for 30 seconds before being quenched in water. The metal plate causes a relatively slow cooling, during which some crystallisation (typically of fluoride) takes place, yielding ultimately a less reactive glass.

G6 is prepared by mixing together 441 parts by weight silica, 232 parts alumina, 130 parts calcium fluoride, 65 parts lithium fluoride, 72 parts aluminium fluoride and 60 parts aluminium phosphate. This is fired at 1300° C., held for 60 minutes, poured onto a metal plate and held there as a melt for 30 seconds before being quenched in water. The resulting glass in each case is ground and sieved, and the fraction of particle size less than 45 microns is deactivated by heating in a furnace at 450° C. for 90 minutes.

Glass modifier: Boron phosphate $BPO_4$ was used in varying concentrations as a glass modifier. It is commercially available in "General Purpose Reagent" grade. It was sieved and the fraction of particle size less than 45 microns was ball-milled with the (previously milled) glass powder for 6 hours to obtain a homogeneous mixture.

Acid: Poly(vinyl phosphonic) acid (PVPA) was synthesised and purified as described in GB-A-2219289.

Prereactant: The PVPA was mixed with a prereactant. The prereactant was incorporated into aqueous solutions of the PVPA by simply heating the PVPA solutions to ≈80° C. on a hot plate and then gradually stirring the prereactant portions into the solutions with the aid of a magnetic stirrer. The white prereactant powder gels up within a few minutes before finally dissolving to result in a homogeneous solution. These solutions were then spray dried and could be stored in resealable bags. Seven different prereactants were tried.

(i) Boron phosphate: improved the compressive strength of the resulting cement. It was however found that, if used instead as a glass modifier, boron phosphate had the additional benefit of lengthening the working time of the cement. Therefore, while boron phosphate is a possible prereactant, we have (when glass is used) preferred to exploit it more fully, as a glass modifier.

(ii) Zinc phosphate:

(iii) Zinc fluoride:

Metal ions appear to crosslink PVPA and hence increase its effective molecular weight or chain length. This in turn improves the compressive strength. Phosphate ions in general improve the working time, giving the cement a longer opportunity to wet the surface on which it has been placed, and hence can improve adhesive strength.

$F^-$ appears to enhance the compressive strength and, by decreasing the surface energy of the cement, improves the wetting power of the newly mixed cement components, hence improving the quality of mixing, hence improving the strength of the cements. Fluoride also desensitises the tooth, and achieves the creation of a new species, conveniently referred to hereafter as PVPA/F, wherein the $F^-$ ions are believed to 'graft' onto the backbone of the PVPA chains. Possible advantages of PVPA/F include the controlled (slow) release of $F^-$ ions and its reduced solubility in water and its 'deactivation' with regards to its reaction with glass to form cements.

(iv) Magnesium fluoride (v) Aluminium fluoride (vi) Stannous fluoride

Divalent metals such as Sn(II) have been found generally better than trivalent. Tin shortens working time (but not excessively) and setting time while improving compressive strength.

(vii) Boron trifluoride.

The PVPA mixed with its prereactant was, as already mentioned, spray dried. Spray drying offers an elegance and simplicity not available with traditional powder:liquid systems. It also avoids the offputting brown colouration associated with PVPA solution. An alternative dewatering method is to freeze-dry the PVPA, but this led to inferior compressive strengths and working times; in addition, freeze-dried PVPA is less stable as it more readily absorbs moisture from the atmosphere. This issue leads naturally to the question of a desiccant.

Desiccant: A problem encountered with all of these formulations is that even spray-dried PVPA readily takes up water from the atmosphere, resulting in inconsistencies unless the PVPA is used within a short space of time. For this reason silica e.g. untreated or preferably hydrophobic silica R972 by Degussa (Wilmslow, Cheshire) was incorporated into PVPA in an attempt to increase its stability and translucency and to improve the handling properties of the cement. The R972 was added as a given percentage of the total PVPA mass. For example if 0.175 g R972 were added to 3.5 g (dry weight) of PVPA then this would be expressed as 5% R972. The desiccant was added directly to the PVPA and mixed using a pestle and mortar.

Complexant: A chelating phosphonic acid (in freeze-dried form) was added to the cement mix (glass+dry PVPA) with the aid of a pestle and mortar. A suitable complexant was Dequest 2010 (trade mark), which is 1-hydroxyethylidene-1,1-diphosphonic acid. This was most successfully handled in freeze-dried form, unlike PVPA. Inadequate chelating phosphonic acid will inadequately lengthen the working time, while excess chelating phosphonic acid will compete with the polymeric phosphonic acid in forming a reaction cement with the glass, the cement formed by "chelating" acid being a source of potential weakness.

Solvent: Distilled water. This would normally be added to the acid, prereactant, dessicant and complexant just before the full cement composition was made up, but other sequences of addition are possible.

The relative proportions of these components are significant, as the following examples will show, and are defined herein according to the following conventions:

The powder:liquid (p/l) ratio is defined as $$\frac{\text{mass of glass powder}}{\text{mass of acid + prereactant + complexant + solvent}}$$

Note that, despite this definition, any of the divisor components (apart from the solvent) can in practice be mixed with the glass powder in the solid phase.

The % strength of acid (e.g. "50% PVPA") is defined as $$\frac{\text{mass of acid + prereactant}}{\text{mass of acid + prereactant + complexant + solvent}} \times 100\%$$

The % strength of complexant (e.g. "15% D2010") is defined as $$\frac{\text{mass of complexant}}{\text{mass of acid + prereactant + complexant + solvent}} \times 100\%$$

Where a desiccant is added to the acid, its mass is added to the divisor in the above definitions, and its own concentration (e.g. "5% hydrophobic silica R972") is defined as $$\frac{\text{mass of desiccant}}{\text{mass of acid}} \times 100\%$$

The expression "mass of glass powder" as used above includes the mass of glass modifier ($BPO_4$). Where we talk (as in the following examples) of, say, "14 g glass/5%$BPO_4$", we thus mean 100 parts (13.333 g) of the product of (silica+alumina+calcium fluoride+cryolite+aluminium phosphate) and 5 parts (0.667 g) of boron phosphate.

In interpreting the examples which follow, the reader will bear in mind that for a cement formulation to count as suitable it has to be comparable with existing dental cement properties. For filling cements this entails a compressive strength of at least 125 MPa and a working and setting time of at least 2½ and 5 minutes respectively. These properties were tested as follows. The solid phase components having been mixed and ground, the solvent (water) was added and the cement formulation mixed. The cement was mixed in batches each containing 1.2 g powder and packed into 6 mm diameter×12 mm height moulds. These were left at 37° C. for one hour, by which time they were set into 6 mm×12 mm pellets. The set pellets were removed and left in distilled water at 37° C. for a further 23 hours.

The compressive strengths of these pellets were found using a crosshead speed of 1 mm per minute. For each cement formulation six pellets were made and the mean and standard deviation of their compressive strengths calculated.

The amount of water added to 1.2 g of powder varies in each formulation and must be calculated. Therefore the actual mass of water added to 1.2 g of powder is found by firstly dividing the total mass of the solid phase by the mass of water in the liquid phase (18.55 g/2.45 g=7.57), and then dividing 1.2 g by the answer obtained (1.2 g/7.57=0.158 g of water).

Working and setting times were ascertained on the Wilson rheometer using two batches of 0.4 g powder with the relevant mass of water, for each cement.

Lastly any formulation which appeared to have promising properties was examined using a Carl Zeiss goniophotometer GP2 fitted with a transistorised voltage stabiliser GTF 6/30 and a mirror galvanometer to ascertain its opacity. This is important as dental cements should resemble the teeth translucency.

In referring to "powder" we mean glass plus glass modifier. In referring to "solid phase" we mean "powder", acid (dry weight), prereactant and complexant for weight/proportion calculation purposes, regardless of the physical state of these components. In referring to "liquid phase", we likewise disregard actual physical state, and mean all the above components except "powder". To clarify, a typical cement composition might contain 3.5 g (dry PVPA/5% $ZnF_2$)+14 g (G5 glass/5% $BPO_4$)+1.05 g complexant D2010+2.45 g water. This would be considered as:

| Solid phase | | Liquid phase | |
| --- | --- | --- | --- |
| PVPA/5% $ZnF_2$ | 3.5 g | 50% PVPA/5% $ZnF_2$ | 3.5 g |
| G5/5% $BPO_4$ | 14.0 g | Water | 2.45 g |
| Freeze dried D2010 | 1.05 g | 15% D2010 | 1.05 g |
| | 18.55 g | | 7.00 g |

The powder to liquid ratio is determined by the mass of glass (=14 g) divided by the total mass of liquid phase (=7 g); therefore the p/l ratio is 2:1. To vary this p/l ratio the mass of the glass/5% $BPO_4$ is altered, while keeping all other parameters constant. For example in a 3:1 p/l ratio, 21 g of glass is used.

The above nominal percentages of PVPA ("50%") and D2010 (15%) are entirely dependent upon their mass in relation to the total mass of the liquid phase.

In the above case, the percentage of PVPA would be calculated as 3.5 g/7.00 g×100%=50% PVPA/5% $ZnF_2$.

Six "liquid-phase's solute" formulations were made, each of which was then made into a cement with three different powder to liquid ratios, viz 2:1, 3:1 and 3.5:1. Powder-to-liquid ratios outside that range were liable to be too difficult to mix or, at the other extreme, too weak in compression. Each of these eighteen was tried with the three different glasses (G4, G5, and G6, each containing 5% $BPO_4$). These six liquid-phase's solute formulations were:

| (1) 50% PVPA/5% $ZnF_2$ with | (a) 15% | D2010 |
| --- | --- | --- |
| | (b) 13.8% | D2010 |
| | (c) 12.5% | D2010 |
| (2) 46% PVPA/5% $ZnF_2$ with | (a) 15% | D2010 |
| | (b) 13.8% | D2010 |
| | (c) 12.5% | D2010 |

A cement may thus be identified, for example, as 1a/2:1/G5.

The results obtained were as follows:

| Example | Working Time (mins) | Setting Time (mins) | Compressive Strength | Standard Deviation |
| --- | --- | --- | --- | --- |
| Comparative (1a/2:1/G5 without $ZnF_2$) | 3.1 | 4.5 | 109 Mpa | 10.1 |
| 1a/2:1/G5 | 2.8 | 4.2 | 138 MPa | 10.4 |
| 1a/2.5:1/G5 | 2.2 | 3.8 | 131 MPa | 13.4 |
| 1a/3:1/G5 | 2.7 | 4.0 | 150 MPa | 14.8 |
| 1b/3:1/G5 | 1.7 | 3.7 | 155 MPa | 11.9 |
| 1b/3:1/G5 | 1.7 | 3.7 | 143 MPa | 11.8 |
| 1b/3:1/G5* | 1.0 | 4.6 | 142 MPa | 7.2 |
| 1c/3:1/G5 | 1.7 | 3.7 | 124 MPa | 10.8 |
| 2a/3:1/G5 | 2.4 | 4.3 | 134 MPa | 8.1 |
| 2b/3:1/G5 | 2.6 | 4.9 | 134 MPa | 10.5 |
| 2c/3:1/G5 | 1.9 | 3.1 | 112 MPa | 13.5 |
| 1b/2:1/G4 | 2.0 | 3.6 | 146 MPa | 13.0 |
| 1b/2:1/G4* | 2.1 | 4.4 | 140 MPa | 10.7 |
| 1b/3:1/G6 | 4.0 | 6.9 | 110 MPa | 12.8 |

*$Zn_3(PO_4)_2$ used in place of $ZnF_2$

| Example | Working Time (mins) | Setting Time (mins) | Compressive Strength | Standard Deviation |
| --- | --- | --- | --- | --- |
| 1b/3:1/G4 but 10% zinc phosphate (no $ZnF_2$) | <1 | 6.7 | 179 MPa | 7.1 |
| 1b/3:1/G5 but 10% zinc phosphate (no $ZnF_2$) | 3.5 | 6.9 | 134 MPa | 7.9 |
| As above - without $BPO_4$ | 1.6 | 3.4 | 95 MPa | 7.0 |
| 1(a)/3:1/G4 but 15% zinc phosphate (no $ZnF_2$) | <1 | 4.2 | 160 MPa | 16.0 |
| 1b/2.5:1/G4 but 10% zinc phosphate (no $ZnF_2$) | 1.5 | 4.4 | 158 MPa | 18.0 |

As the percentage of hydrophobic silica R972 as desiccant within the cement increases, both the working and setting times fall, but paradoxically the more R972, the smaller this fall. R972 incorporation up to an optimum value of 5% also increases the compressive strength, after which the effect is less.

The opacity is unaffected by R972 except at higher concentrations.

Summarising some of the trends observable from the examples and elsewhere:

Freeze-dried PVPA is less stable than spray-dried PVPA and gives lower compressive strength and working times.

Zinc phosphate used in 7½ and 10% concentrations give better working times than 5% or 15%, but 10% gives a quicker set.

Compressive strength was however best at 12½%.

Increasing boron phosphate in the glass lengthens working time and setting time and lowers compressive strength. As to this, four experiments on glass G5 with 0, 5%, 10% and 15% $BPO_4$ respectively, added to PVPA+20%D2010 at a powder:liquid ratio of 5:1, yielded the results:

| BPO₄ | Working time | Compressive Strength after 24 h | |
|---|---|---|---|
| | | Dry storage | Wet storage |
| 0% | under 1 minute | 130 MPa | 100 MPa |
| 5% | 3.1 min | 85 MPa | 35 MPa |
| 10% | 2.3 min | 130 MPa | 110 MPa |
| 15% | 3.3 min | 160 MPa | 110 MPa |

Other results on the PVPA reactant are as follows:

Further results were obtained using PVPA concentrations of 60 weight % and Dequest 2010 concentrations of 15% in the liquid. This level of PVPA appeared to be detrimental to compressive strength, while this level of Dequest 2010 had a mildly beneficial effect on compressive strength and a significantly beneficial effect in extending the working time of the cement while sharpening its set, as shown in Table 3. The sharper the set (i.e. the lower the ratio ST/WT), the less the resulting cement is likely to weaken on early exposure to oral fluid (water).

In Tables 1, 2 and 3, the glass used was G5.

TABLE 3

| Cement Formulation | Working Time | Setting Time | ST/WT |
|---|---|---|---|
| 50% PVPA, 5% ZnF₂ + 10% D2010 | 114 sec | 252 sec | 2.2 |
| 50% PVPA, 5% ZnF₂ + 15% D2010 | 174 sec | 333 sec | 1.9 |

TABLE 1

COMPRESSIVE STRENGTHS (MPa) OF VARIOUS GLASS-POLY(VINYL PHOSPHONIC ACID) CEMENTS.

| | p/l | % zinc fluoride incorporated | | | | | | |
|---|---|---|---|---|---|---|---|---|
| | | 0 | 5 | 10 | 12½ | 15 | 20 | 25 |
| 30% PVPA, 7½% D2010, | 1.5:1 | 24.6 (3.1) | — | 62.1 (8.0) | 29.1 (3.7) | 30.0 (6.8) | 19.7 (2.3) | 17.5 (3.5) |
| 30% PVPA, 10% D2010, | 2:1 | 47.8 (4.9) | — | 50.7 (4.8) | 45.3 (2.8) | 39.2 (5.1) | 44.3 (4.9) | 44.1 (7.1) |
| 40% PVPA, 7½% D2010, | 2:1 | 80.8 (6.5) | — | — | 79.0 (7.0) | 66.7 (6.3) | 66.8 (5.7) | 48.1 (9.0) |
| 40% PVPA, 10% D2010, | 2:1 | 83.7 (7.6) | 92.2* (6.4) | 102.6 (8.0) | 89.4 (4.0) | — | 85.7 (5.0) | 83.5 (9.1) |
| 50% PVPA, 10% D2010, | 1.4:1 | 120.9 (13.9) | 139.4* (10.0) | 147.1 (10.5) | 135.1 (9.3) | 139.4 (8.9) | 117.3 (8.9) | 126.6 (12.9) |
| 50% PVPA, 15% D2010, | 1.4:1 | 117.7* (14.7) | 141.5* (10.2) | 140.7* (5.9) | | | | |
| 60% PVPA, 15% D2010, | 1.4:1 | — | 76.0* (9.0) | — | | | | |

The bracketed numbers represent the standard deviations of six cement specimens for each formulation.
*Obtained using a presumed inferior batch of glass.

TABLE 2

THE WORKING AND SETTING TIMES OF GLASS-POLY(VINYL PHOSPHONIC ACID) CEMENTS.

| CEMENT FORMULATION | p/l | Working Times (Setting Times) - in seconds % ZnF₂ incorporated | | | | | |
|---|---|---|---|---|---|---|---|
| | | 0% | 5% | 10% | 15% | 20% | 25% |
| 30% PVPA, 7½% D2010, | 1.5:1 | — | — | 98 (252) | 114 (260) | 101 (246) | 129 (516) |
| 30% PVPA, 10% D2010, | 2:1 | 99 (202) | — | 104 (249) | 120 (279) | 125 (360) | 114 (262) |
| 40% PVPA, 7½% D2010, | 2:1 | 74 (141) | — | — | 79 (137) | 93 (176) | 92 (144) |
| 40% PVPA, 10% D2010, | 2:1 | 98 (197) | — | 83 | — (155) | 111 (154) | 87 (201) |
| 50% PVPA, 10% D2010, | 1.4:1 | 104 (174) | 114 (252) | 99 (210) | 111 (210) | 108 (216) | 114 (207) |

EXAMPLE 1

This is an example of a 5% ZnF₂-modified 50% PVPA with 15% D2010, used in a p/l ratio of 1.4:1 with G5 glass.

The modified PVPA was prepared by adding $ZnF_2$ to an aqueous solution of PVPA (40% by mass) to give a $ZnF_2$ level of 5% on PVPA. This mixture was heated at 80° C. until all of the $ZnF_2$ had dissolved (approximately 2 hrs), then cooled and the solid product obtained by spray-drying. This solid was then blended with an appropriate amount of freeze-dried D2010 and glass powder in a pestle and mortar. Cements were prepared by adding sufficient water to create an equivalent powder/liquid ratio of 1.4:1.

The resulting cement had the following properties:
Working time: 174 seconds
Setting time: 333 seconds
Compressive strength: 152.8 MPa This comfortably meets British Standard 6039:1981 for glass polyalkenoate filling cements (WT<2¾ minutes, ST <5 minutes, CS>125 MPa), and can be compared with a comparative cement, exactly as above but The results presented below were obtained with a Wilson rheometer at room temperature.
The results are average values of three cement samples. (Setting times are in brackets.)

with no zinc fluoride:
Working time: 165 seconds
Setting time: 296 seconds
Compressive strength: 118-123 MPa

EXAMPLE 2

The same procedure was followed as in Example 1, except that in place of the zinc fluoride, Example 2 used magnesium fluoride $MgF_2$. The compressive strengths of the resulting cements were as follows:

| Cement Formulation | p:l | Compressive Strengths of Cements (MPa) % $MgF_2$ Incorporated | | | |
|---|---|---|---|---|---|
| | | 0% | 2½% | 5% | 10% |
| 40% PVPA, 10% D2010, | 2:1 | 56.79 (6.86) | 80.74 (6.13) | 94.02 (13.67) | 68.93 (5.06) |
| 40% PVPA, 15% D2010, | 2:1 | 78.39 (8.79) | 95.36 (8.66) | 98.43 (12.71) | 91.42 (17.63) |
| 50% PVPA, 10% D2010, | 1.4:1 | 103.63 (11.39) | 93.83 (9.67) | 107.72 (8.80) | 108.62 (13.42) |
| 50% PVPA, 15% D2010, | 1.4:1 | 123.05 (10.91) | 128.38 (13.21) | 114.81 (11.54) | 128.32 (6.86) |

(The figures in brackets are the standard deviation of six results of each cement formulation.)

The working and setting times of these cements were obtained as with the working and setting time results of Example 1, and were as follows:

| Cement formulation | p/l | Working Times (Setting Times) (seconds) % $MgF_2$ Incorporation | | | |
|---|---|---|---|---|---|
| | | 0% | 2½% | 5% | 10% |
| 40% PVPA, 10% D2010, | 2:1 | 108 (240) | 96 (216) | 98 (207) | 117 (269) |
| 40% PVPA, 15% D2010, | 2:1 | 112 (203) | 131 (263) | 107 (227) | 108 (263) |
| 50% PVPA, 10% D2010, | 1.4:1 | 114 (240) | 125 (291) | 110 (263) | 109 (278) |
| 50% PVPA, 15% D2010, | 1.4:1 | 180 (321) | 168 (324) | 129 (282) | 130 (294) |

The results with 15% D2010 (compared with 10% D2010) indicated not only better strength but also a desirable reduction in the ratio (working time)/(setting time). Taking all these properties, the best "MgF2" sample was 50% PVPA, 2½%$MgF_2$, 15% D2010, p/l=1.4:1.

EXAMPLE 3

Example 1 was repeated but using aluminum fluoride $AlF_3$ in place of $ZnF_2$. Increasing $AlF_3$ led to increasing strength but cements with $AlF_3$ greater than 5% were not tested due to the difficulty encountered in mixing such cement formulations. There is an increase of approximately 17% in compressive strength of cements made from PVPA with 5% $AlF_3$ incorporation compared to those from pure PVPA. This is significant having regard to the standard deviations of these cements. Cements having 15% D2010 concentration also show an improvement in compressive strength compared with 10% D2010 variant. As with the $ZnF_2$-modified cements of Example 1, $AlF_3$-modified PVPA cements with 60% PVPA are weak.

Working times and setting times decreased more or less in step as the $AlF_3$ concentration was increased, and considering all the properties, the best all-round "$AlF_3$" sample was 50% PVPA, 2½% $AlF_3$, 15% D2010, p/l=1.4:1, yielding:
  Working Time: 134 seconds
  Setting Time: 246 seconds
  ST/WT: 1.8
  Compressive Strength: 132 MPa
Individual properties could be bettered, for example the compressive strength could be improved to 137 MPa using 5% $AlF_3$, but at the cost of a working time cut to 108 seconds and an ST/WT of 2.1.

EXAMPLE 4

This Example shows the use of ZnO rather than glass. ZnO, even after heat treatment, is too reactive with PVPA and was therefore presented in a modified form as follows.

Water was mixed for 5 minutes with 0.02 g sodium dodecyl benzene sulphonate surfactant. After each one of the following additions, a further (at least) 15 minutes' mixing was performed: 0.67g xanthan gum (mill grade) gelling agent, then 12.50g $ZnF_2$, then 4.00g Kaolin (mixed 20 minutes), then 83.50 g zinc oxide (general purpose grade) (mixed ¾ hour).

The resulting slurry was left to gel in a cuboidal mould for 2 days then dried in an oven at 105° C. for 2 days. The resulting oxide brick was heated to 1200° C. for 8 hours and cooled over a day. The brick was ground for as short a period as possible and sieved to obtain −45 microns powder; it was preferred to lose oxide on the sieve than to grind for so long that an excess of submicron powder resulted, as such submicron powder would have been too reactive.

This zinc oxide powder was reacted in p:l ratio of 1.5:1 with aqueous PVPA of 50% strength with 13.8% D2010, the PVPA having been pre-reacted with 10% $BPO_4$. This yielded a cement with a working time of 65 seconds, a setting time of 190 seconds and a compressive strength of 52 MPa. This cement should be capable of releasing fluoride ions, which is Known to be clinically beneficial.

EXAMPLE 5

This Example shows a two-paste system. Using 10% $Zn_3(PO_4)_2$-modified PVPA (40 g), and a commercial 60% aqueous solution of D2010 (13.15g), and 4 g added water, made into a solution, a thick tacky paste was formed by letting the solution stand for 3 weeks. The overall weight composition, after allowing for the fact that 40% of the 13.15 g component was itself water, worked out at 70.0% PVPA+13.8% D2010+16.2% water. Hydrophobic silica could also be added. This unusually concentrated PVPA helped to achieve a thick paste with plenty of active ingredient and also compensated for the presence of water in the glass paste, which is now described.

20 g G5 glass (not deactivated by heat-treatment or acid washing) was mixed with 0.11g carboxymethylcellulose thickener and 6.89 g water. These were the least quantities of thickener and of water that allowed the glass to be presented as a paste; larger quantities of thickener and/or of water led to a weaker cement; but possibly de-activated G5 glass would need less water.

A cement was made using a glass:polymer ratio of 2.5:1 and had a compressive strength of 48 MPa.

EXAMPLE 6

This example shows results from PVPA prereacted with $SnF_2$ and with $BF_3$, reacted with G6 glass. All these PVPA solutions contained 13.8% Dequest D2010.

TABLE 3

| | WORKING TIME (mins) | SETTING TIME (mins) | COMPRESSIVE STRENGTH (MPa) |
|---|---|---|---|
| PVPA not | 2.95 | 5.05 | 85.7 ± 15 |

TABLE 3-continued

| | WORKING TIME (mins) | SETTING TIME (mins) | COMPRESSIVE STRENGTH (MPa) |
|---|---|---|---|
| pre-reacted PVPA + 2.5% SnF$_2$ | 2.30 | 4.95 | 85.6 ± 27 |
| PVPA + 5% SnF$_2$ | 1.67 | 3.00 | 116.8 ± 23 |
| PVPA + 10% SnF$_2$ | 1.83 | 3.30 | 89.9 ± 6 |
| PVPA + 2.5% BF$_3$ | 2.45 | 5.00 | 109.6 ± 7 |
| PVPA + 5% BF$_3$ | 3.10 | 5.30 | 68.3 ± 19 |
| PVPA + 10% BF$_3$ | 2.08 | 4.00 | 124.6 ± 32 |

The BF$_3$ and also the SnF$_2$ improved working time, setting time and compressive strength compared with the non-pre-reacted PVPA. The PVPA was pre-reacted as in the previous examples, but note that BF$_3$ was used in the form of BF$_3$·2H$_2$O, which is a liquid.

We claim:

1. A cement composition, comprising an intimately blended mixture of a water-containing liquid, at least 30% by weight of the composition being a cation-catalysed cross-linkable polymeric acid containing on average one phosphonic acid group per one to three backbone carbon atoms, and a metal oxide or cation-leachable surgically acceptable aluminosilicate glass powder in the proportions (1 minus x)g said polymeric acid: 1 to 5 g glass or metal oxide: x g liquid, where x is from 0.3 to 0.7, wherein said polymeric acid has been pre-reacted in aqueous solution at elevated temperature with a fluoride, phosphate and mixtures thereof.

2. A cement composition according to claim 1, wherein the said polymeric acid is poly(vinyl phosphonic acid).

3. A cement composition according to claim 2, wherein the acid additionally contains poly(acrylic acid).

4. A cement composition according to claim 1, wherein the metal oxide is ZnO or MgO.

5. A cement composition according to claim 1, wherein the glass is a fluoroaluminosilicate.

6. A cement composition according to claim 1, wherein the glass powder contains SiO$_2$ and Al$_2$O$_3$ in the mass proportions (0.6 to 3.0):1.

7. A cement composition according to claim 6, wherein the mass proportion SiO$_2$:Al$_2$O$_3$ is (1 to 2):1.

8. A cement composition according to claim 1, wherein the fluoride or phosphate with which the acid has been pre-reacted is of a divalent or trivalent metal.

9. A cement composition according to claim 8, wherein the said divalent or trivalent metal is any of Zn, Sn, Mg, Ca, Al or B, or a mixture thereof.

10. A cement composition according to claim 9, wherein the acid has been pre-reacted with ZnF$_2$ and BPO$_4$.

11. A cement composition according to claim 1, wherein the fluoride or phosphate with which the acid has been pre-reacted amounts to 2½ to 12½% by weight of said acid.

12. A cement composition according to claim 1 wherein the glass powder is two-phase.

13. A cement composition according to claim 1, wherein the glass powder consists of particles substantially all of which are smaller than 100 microns.

14. A cement composition according to claim 1, wherein the glass powder is admixed with boron phosphate.

15. A cement composition according to claim 14, wherein the admixed boron phosphate amounts to at least 10 wt % based on the glass.

16. A cement composition according to claim 1, wherein a chelating agent is present.

17. A cement composition according to claim 16, wherein the chelating agent is a chelating phosphonic acid.

18. A mixture of dried pre-reacted polymeric acid containing on average one phosphonic acid group per one to three backbone carbon atoms, and a metal oxide or cation-leachable surgically acceptable aluminosilicate glass powder in the proportions (1 minus x)g said polymeric acid: 1 to 5 g glass or metal oxide: x g liquid, where x is from 0.3 to 0.7, wherein said polymeric acid is pre-reacted in an aqueous solution at elevated temperature with a fluoride, phosphate and mixtures thereof.

19. A mixture according to claim 18, further comprising a desiccant.

20. A mixture according to claim 18, packed in a sealed capsule.

21. A two-pack system comprising a mixture according to claim 20 and a capsule of liquid such that the contents of the two capsules when mixed yield a cement.

22. A two-pack system comprising a first paste comprising a pre-reacted polymeric acid and a second paste comprising a metal oxide or glass powder, such that the two pastes when mixed yield a cement, said prereacted polymeric acid and said second paste comprising said metal oxide or glass powder being as defined in claim 1.

* * * * *